(12) United States Patent
Brown

(10) Patent No.: US 7,374,782 B2
(45) Date of Patent: May 20, 2008

(54) PRODUCTION OF MICROSPHERES

(75) Inventor: Larry R. Brown, Newton, MA (US)

(73) Assignees: Baxter International Inc., Deerfield, IL (US); Baxter Healthcare S.A. (CH)

( * ) Notice: Subject to any disclaimer, the term of this patent is extended or adjusted under 35 U.S.C. 154(b) by 382 days.

(21) Appl. No.: 10/399,829

(22) PCT Filed: Oct. 25, 2001

(86) PCT No.: PCT/US01/51166

§ 371 (c)(1),
(2), (4) Date: Oct. 10, 2003

(87) PCT Pub. No.: WO02/43580

PCT Pub. Date: Jun. 6, 2002

(65) Prior Publication Data

US 2004/0043077 A1    Mar. 4, 2004

Related U.S. Application Data

(60) Provisional application No. 60/244,098, filed on Oct. 27, 2000.

(51) Int. Cl.
*A61K 9/14*          (2006.01)
(52) U.S. Cl. .................................... 424/489
(58) Field of Classification Search ................ 424/489
See application file for complete search history.

(56) References Cited

U.S. PATENT DOCUMENTS

| | | |
|---|---|---|
| 3,219,533 A | 11/1965 | Mullins |
| 3,737,337 A | 6/1973 | Schnoring et al. |
| 3,891,570 A | 6/1975 | Fukushima et al. |
| 4,083,831 A * | 4/1978 | Santosusso ................ 528/52 |
| 4,389,330 A | 6/1983 | Tice et al. |
| 4,530,840 A | 7/1985 | Tice et al. |
| 4,612,008 A | 9/1986 | Wong et al. |
| 4,652,441 A | 3/1987 | Okada et al. |
| 4,728,721 A | 3/1988 | Yamamoto et al. |
| 4,744,933 A | 5/1988 | Rha et al. |
| 4,818,542 A | 4/1989 | DeLuca et al. |
| 4,849,228 A | 7/1989 | Yamamoto et al. |
| 4,861,627 A | 8/1989 | Mathiowitz et al. |
| 4,897,268 A | 1/1990 | Tice et al. |
| 4,904,479 A | 2/1990 | Illum |
| 4,917,893 A | 4/1990 | Okada et al. |
| 4,925,677 A | 5/1990 | Feijen |
| 5,008,116 A | 4/1991 | Cahn |
| 5,075,109 A | 12/1991 | Tice et al. |
| 5,102,872 A | 4/1992 | Singh et al. |
| 5,149,543 A | 9/1992 | Cohen et al. |
| 5,160,745 A | 11/1992 | DeLuca et al. |
| 5,204,108 A | 4/1993 | Illum |
| 5,213,788 A | 5/1993 | Ranney |
| 5,213,812 A | 5/1993 | Ruiz |
| 5,300,464 A | 4/1994 | Rittler |
| 5,330,768 A | 7/1994 | Park et al. |
| 5,360,610 A | 11/1994 | Tice et al. |
| 5,384,133 A | 1/1995 | Boyes et al. |
| 5,407,609 A | 4/1995 | Tice et al. |
| 5,417,986 A | 5/1995 | Reid et al. |
| 5,422,120 A | 6/1995 | Kim |
| 5,476,663 A | 12/1995 | Okada et al. |
| 5,480,656 A | 1/1996 | Okada et al. |
| 5,482,927 A | 1/1996 | Maniar et al. |
| 5,543,158 A | 8/1996 | Gref et al. |
| 5,556,642 A | 9/1996 | Kobayashi et al. |
| 5,573,934 A | 11/1996 | Hubbell et al. |
| 5,575,987 A | 11/1996 | Kamei et al. |
| 5,578,709 A | 11/1996 | Woiszwillo |
| 5,595,760 A | 1/1997 | Cherif-Cheikh |
| 5,599,719 A | 2/1997 | Woiszwillo |
| 5,603,961 A | 2/1997 | Suzuki et al. |
| 5,631,020 A | 5/1997 | Okada et al. |
| 5,631,021 A | 5/1997 | Okada et al. |
| 5,637,309 A | 6/1997 | Tajima et al. |
| 5,643,607 A | 7/1997 | Okada et al. |
| 5,650,173 A | 7/1997 | Ramstack et al. |
| 5,654,008 A | 8/1997 | Herbert et al. |
| 5,654,010 A | 8/1997 | Johnson et al. |
| 5,674,521 A | 10/1997 | Gehrke et al. |
| 5,851,451 A | 12/1998 | Takechi et al. |
| 5,932,248 A | 8/1999 | Chen et al. |
| 5,945,126 A | 8/1999 | Thanoo et al. |
| 5,981,719 A * | 11/1999 | Woiszwillo et al. ........ 530/410 |
| 5,989,463 A | 11/1999 | Tracy et al. |
| 6,036,976 A | 3/2000 | Takechi et al. |
| 6,090,925 A | 7/2000 | Woiszwillo |
| 6,120,787 A | 9/2000 | Gustafsson et al. |
| 6,153,211 A | 11/2000 | Hubbell et al. |
| 6,265,389 B1 | 7/2001 | Burke |
| 6,268,053 B1 | 7/2001 | Woiszwillo et al. |

(Continued)

FOREIGN PATENT DOCUMENTS

CA          2157793 A1    9/1994

(Continued)

OTHER PUBLICATIONS

Arshady et al., "Preperation of poly nano- and microspheres by vinyl polymerization techinques," J. Microencapsulation, 1988, vol. 5, No. 2, 101-114.*

(Continued)

*Primary Examiner*—Michael Woodward
*Assistant Examiner*—Bethany Barham
(74) *Attorney, Agent, or Firm*—Marshall, Gerstein & Borun, LLP

(57) ABSTRACT

Protein microspheres are produced by contacting an aqueous solution of a macromolecule and a polymer with a surface at a high surface area to volume ratio, and heating the solution. The microspheres are useful for preparing pharmaceuticals of defined dimensions which can be delivered to a patient by inhalation therapy.

36 Claims, 7 Drawing Sheets

U.S. PATENT DOCUMENTS

| | | |
|---|---|---|
| 6,270,795 B1 | 8/2001 | Jones et al. |
| 6,270,802 B1 | 8/2001 | Thanoo et al. |
| 6,361,798 B1 | 3/2002 | Thanoo et al. |
| 6,395,253 B2 | 5/2002 | Levy et al. |
| 6,395,300 B1 | 5/2002 | Straub et al. |
| 6,395,302 B1 | 5/2002 | Hennink et al. |
| 6,455,074 B1 | 9/2002 | Tracy et al. |
| 6,458,387 B1 | 10/2002 | Scott et al. |
| 6,475,468 B2 | 11/2002 | Zhu et al. |
| 6,475,995 B1 | 11/2002 | Roy et al. |
| 6,506,410 B1 | 1/2003 | Park et al. |
| 6,596,316 B2 | 7/2003 | Lyons et al. |
| 6,749,866 B2 | 6/2004 | Bernstein et al. |
| 6,814,980 B2 | 11/2004 | Levy et al. |
| 6,830,737 B2 | 12/2004 | Ramstack |
| 6,861,064 B1 | 3/2005 | Laakso et al. |
| 2001/0002261 A1 | 5/2001 | Morrison et al. |
| 2001/0007853 A1 | 7/2001 | Dimarchi et al. |
| 2002/0146459 A1 | 10/2002 | Levy et al. |
| 2003/0007990 A1 | 1/2003 | Blankenship et al. |
| 2003/0059474 A1 | 3/2003 | Scott et al. |
| 2003/0064033 A1 | 4/2003 | Brown et al. |
| 2004/0014698 A1 | 1/2004 | Hortelano et al. |
| 2004/0043076 A1 | 3/2004 | Dulieu et al. |
| 2004/0091541 A1 | 5/2004 | Unger |
| 2005/0048127 A1 | 3/2005 | Brown et al. |
| 2005/0147687 A1 | 7/2005 | Rashba-Step et al. |

FOREIGN PATENT DOCUMENTS

| | | |
|---|---|---|
| EP | 0 248 531 A2 | 12/1987 |
| EP | 0 351 296 A1 | 1/1990 |
| EP | 0 357 401 A2 | 3/1990 |
| EP | 0 809 110 A1 | 11/1997 |
| EP | 1 060 741 A1 | 12/2000 |
| JP | 08-225454 | 9/1996 |
| WO | WO 93/11743 A1 | 6/1993 |
| WO | WO 93/11744 A1 | 6/1993 |
| WO | WO 93/11745 A1 | 6/1993 |
| WO | WO 94/07514 A1 | 4/1994 |
| WO | WO 94/18947 | 9/1994 |
| WO | WO 94/20856 | 9/1994 |
| WO | WO 96/19197 A1 | 6/1996 |
| WO | WO 99/48479 A | 9/1999 |
| WO | WO 00/00215 A1 | 1/2000 |
| WO | WO 01/05379 | 1/2001 |
| WO | WO 01/28524 A1 | 4/2001 |
| WO | WO 02/43580 A1 | 6/2002 |
| WO | WO 03/015750 A1 | 2/2003 |

OTHER PUBLICATIONS

Sefton et al., "Ethylene-Vinyl Acetate Copolymer Microspheres for Controlled Release of Macromolecules," 1984, J. Pharmaceutical Sciences, vol. 73, No. 12, 1859-1861.*

Adjei et al., Bioavailability of Leuprolide Acetate Following Nasal and Inhalation Delivery to Rats and Healthy Humans, *Pharm. Res.*, vol. 9, No. 2, pp. 244-249 (1992).

Ahn et al., Biodegradable poly(ethylenimine) for plasmid DNA delivery, *Journal of Controlled Release*, (2002), vol. 80 (1-3), pp. 273-282.

Arshady, Preperation of polymer nano- and microspheres by vinyl polymerization techniques, *J. Microencapsulation*, (1988), vol. 5, No. 2, pp. 101-114.

Banchereau et al., Dendritic cells and the control of immunity, *Nature*, (1998), vol. 392, pp. 245-252.

Berton et al., Improved oligonucleotide uptake and stability by a new drug carrier, the SupraMolecular BioVector (SMBV), *Biochimica Biophysica Acta*, (1997), vol. 1355, pp. 7-19.

Bisker-Leib et al., Uniform Microsphere Formation from Small Organic Molecules, Transac. of the 31st Control. *Rel. Soc. Annual Meeting*, (2004), #631A.

Bisker-Leib et al., Anti-Factor VII Monoclonal Antibody Microspheres, in Proceed. of the 2004- *Amer. Assoc. of Pharm. Scs Natl. Biotech. Conference*, (2004), p. 76.

Boussif et al., A versatile vector for gene and oligonucleotide transfer into cells in culture and *in vivo*: Polyethylenimine, *Proc. Natl. Acad. Sci. (U.S.A).*, (1995), vol. 92, pp. 7297-7301.

Brazeau et al., *In vitro* myotoxicity of selected cationic macromolecules used in non-viral gene delivery,*Pharmaceutical Research*, (1998), vol. 15(5), pp. 680-684.

Brown et al., Pulmonary Delivery of Novel Insulin Microspheres, *Proceed, Respiratory Drug Delivery VIII*, (2002), pp. 431-434.

Brown et al., PROMAXX Microsphere Characterization, *Proceed, Respiratory Drug Delivery LX*, (2004), pp. 477-479.

Brown et al., Tetrafluoroethane (HFC 134A) Propellant-Drive Aerosols of Proteins, *Pharm. Res.*, 14(11): 1542-1547, (1997).

Brown et al. Propellant-Driven Aerosols for Delivery of Proteins in the Respiratory Tract, *J. Aerosol Med.*, vol. 8, No. 1 43-58 (1995).

Brown et al., Propellant-driven Aerosols of Functional Proteins as Potential Therapeutic Agents in the Respiratory Tract, *Immunopharmacology*, vol. 28, 241-257 (1994).

Bustami et al., Generation of micro-particles of proteins for aerosol delivery using high pressure modified carbon dioxide, *Pharmaceutical Research*, (2000), vol. 17, No. 11, pp. 1360-1366.

Byrne et al., Dendritic cells: making progress with tumour regression? *Immunology and Cell Biology*, (2002), vol. 80, pp. 520-530.

Chamarthy et al., A cationic peptide consists of ornithine and histidine repeats augments gene transfer in dendritic cells, *Molecular Immunology*, (2003), vol. 40(8), pp. 483-490.

Chollet et al, Side-effects of a systemic injection of linear polyethylenimine-DNA complexes, *Journal of Gene Medicine*, (2002), vol. 4, pp. 84-91.

Chu et al., Efficiency of cytoplasmic delivery by pH-sensitive liposomes to cells in culture, *Pharm. Res.*, (1990), vol. 7, pp. 824-834.

Couvreur et al., pH-sensitive liposomes: an intelligent design system for the delivery of antisense oligonucleotides. *J. Liposome Res.*, (1997), vol. 7, pp. 1-18.

Crystal, Transfer of genes to humans: early lessons and obstacles for success, *Science*, (1995), vol. 270, pp. 404-410.

Dokka et al., Inhibition of endotoxin-induced lung inflammation by interleukin-10 gene transfer in mice, *Am J Physiol Lung Cell Mol Physiol*, (2000), vol. 279(5), pp. L872-L877.

Felgner et al., Cationic liposome-mediated transfection, (1989), *Nature*, vol. 337, pp. 387-388.

Glorioso et al., Development of Herpes Simplex virus vectors for gene transfer to the central nervous system, in *Gene Therapeutics: Methods and Applications of Direct Gene Transfer*, (1993), pp. 281-302.

Hudson et al., Biodegradable polymer matrices for the sustained exogenous delivery of a biologically active c-*myc* hammerhead ribozyme, *Int. J. Pharm.*, (1996), vol. 136, pp. 23-29.

Hughes et al., Evaluation of adjuvants that enhance the effectiveness of antisense oligodeoxynucleotides., *Pharm. Res.*, (1996), vol. 13, pp. 404-410.

Hwang et al., Cationic polymers for gene delivery: designs for overcoming barriers to systemic administration, *Curr. Opin. Mol. Ther.*, (2001), vol. 3, pp. 183-191.

Kabanov et al., Water-soluble block polycations as carriers for oligonucleotide delivery, *Bioconjugate Chem.*, (1995), vol. 6, pp. 639-647.

Kataoka et al., Spontaneous formation of polyion complex micelles with narrow distribution from antisense oligonucleotide and cationic block copolymer in physiological saline, *Macromolecules*, (1996), vol. 29, pp. 8556-8557.

Lee et al., Development of an Aerosol Dosage Form Containing Insulin, *J. Pharm. Sci.*, 65(4): 567-572, (1976).

Legendre, Delivery of plasmid DNA into mammalian cell lines using pH-sensitive liposomes: comparison with cationic liposomes, *Pharm. Res.* (1992), vol. 9, pp. 1235-1242.

Loke et al., Delivery of c-myc antisense phosphorothioate oligodeoxynucleotides to hematopoietic cells in culture by liposome fusion: specific reduction in c-myc protein expression correlates with inhibition of cell growth and DNA synthesis, *Curr. Top. Microbiol. Immunol.*, (1998), vol. 141, pp. 282-289.

Mahato et al., Cationic lipid-based gene delivery systems: pharmaceutical perspectives, *Pharm. Res.*, (1997), vol. 14, pp. 853-859.

Meiri et al., Reversible antisense inhibition of Shaker-like Kv1.1 potassium channel expression impairs associative memory in mouse and rat, *Proc. Natl. Acad. Sci. U.S.A.*, (1997), vol. 94, pp. 4430-4434.

Middaugh, Oligonucleotide delivery, *Encyclopedia of Controlled Drug Delivery*, vol. 2, (1999), pp. 691-697.

Miller, Human gene therapy comes of age, *Nature*, (1992), vol. 357, pp. 455-460.

Moghimi, Chemical camouflage of nanospheres with a poorly reactive surface: towards development of stealth and target-specific nanocarriers, *Biochimica et Biophysica Acta*, vol. 1590, pp. 131-139, (2002).

Morita et al., Formation and Isolation of Spherical Fine Protein Microparticles Through Lyophilization of Protein-Poly (ethylene Glycol) Aqueous Mixture, *Pharmaceutical Research*, (2000), vol. 17, No. 11, pp. 1367-1373.

Myrdal, Optimized Dose Delivery of the Peptide Cyclosporine Using Hydrofluoroalkane-Based Metered Dose Inhalers, *J. Pharm. Sci.*, vol. 93, No. 4, 1054-1061 (2004).

Nakate, Improvement of Pulmonary Absorption of Cyclopeptide FK224 in rats by co-formulating with β-cyclodextrin, *EP J. of Pharm. and Biopharm.* 55 147-154 (2003).

Oberhauser et al., Enhancing endosomal exit of nucleic acids using pH-sensitive viral fusion peptides, In: Delivery Strategies for Antisense Oligonucleotides *Therapeutics, Ed.* Akhtar, S., (1995), pp. 247-266.

Perlaky et al. Growth inhibition of human tumor cell lines by antisense oligonucleotides designed to inhibit p 120 expression, *Anti-Cancer Drug Des.*, (1993), vol. 8, pp. 3-14.

Radler et al., Structure of DNA-cationic liposome complexes: DNA intercalation in multilamellar membranes in distinct interhelical packing regimes, *Science*, (1997), vol. 275, pp. 810-814.

Rashba-Step et al., Albumin Microspheres as Drug Delivery Vehicle for Multiple Routes of Administration, *Proceed. Int'l. Symp. Control. Rel. Bioact. Materials*, (2001), 1001-1002, vol. 28.

Rashba-Step et al., PROMAXX Protein Matrix Microspheres for Delivery of Alpha-1 Antitrypsin Via the Pulmonary Route, Transac. of the 31st Control. *Rel. Soc. Annual Meeting*, (2004), #474.

Sah et al., Biodegradable microcapsules prepared by a w/o/w technique: effects of shear force to make a primary w/o emulsion on their morphology and protein release, *J. of Microencapsulation*, (1995), vol. 12, No., pp. 59-69.

Schwartz et al., Synthetic DNA-compacting peptides derived from human sequence enhance cationic lipid-mediated gene transfer in vitro and in vivo, *Gene Therapy*, (1999), vol. 6, pp. 282-292.

Sefton et al., Ethylene-Vinyl Acetate Copolymer Microsphere for Controlled Release of Macromolecules, (1984), *J. Pharm. Sciences*, vol. 73, No. 12 1859-1861.

Sinha, et al., Biodegradable microspheres for protein delivery, *Journal of Controlled Release*, (2003), vol. 90, pp. 261-280.

Sweeney et al, Efficient therapeutic gene delivery after systemic administration of a novel polyethylenimine/DNA vector in an orthotopic bladder cancer model, *Cancer Res.* (2003), vol. 63, pp. 4017-4020.

Thierry, et al. Overcoming multidrug resistance in human tumor cells using free and liposomally encapsulated antisense oligodeoxynucleotides, *Biochem, Biophys. Res. Commun.*, (1993), vol. 190, pp. 952-960.

Tiyaboonchai, et al., Formulation and characterization of DNA-polyethylenimine-dextran sulfate nanoparticles, *European Journal of Pharmaceutical Sciences*, (2003), vol. 19, pp. 191-202.

Tomlinson, et al., Controllable gene therapy Pharmaceutics of non-viral gene delivery systems *J. Controlled Release*, (1996), vol. 39, pp. 357-372.

Vanderkerken et al, Synthesis and evaluation of poly(ethylene glycol)-polylysine block copolymers as carriers for gene delivery, *J. Bioactive and Compatible Polymers*, 2000, vol. 15, pp. 115-138.

Yamakawa, et al., Release behavior of poly(lactic acid-co-glycolic acid) implants containing phosphorothioate oligodeoxynucleotide, *Biol. Pharm. Bull.*, (1997), vol. 20, pp. 455-459.

Yang, et al., Crystalline monoclonal antibodies for subcutaneous delivery, *Proc. Natl. Acad. Sci (USA)*, (2003), vol. 100, No. 12, pp. 6934-6939.

Zelphati et al, Mechanism of oligonucleotide release from cationic lipids, *Proc. Natl. Acad. Sci (USA)*, (1996), vol. 100, No. 12, pp. 11493-11498.

Zhao, et al., Modulation of oligonucleotide-induced immune stimulation by cyclodextrin analogs, *Biochem. Pharmacol.*, (1996), vol. 52, pp. 1537-1544.

International Application/International Search Report from International Application No. PCTUS01/51166, Mailing date: Jun. 6, 2002.

International Searching Authority/Written Opinion from International Application No. PCT/US2005/016660, Mailing Date: Sep. 27, 2005.

International Searching Authority/Written Opinion from International Application No. PCT/US2005/016651, Mailing Date: Sep. 5, 2005.

International Searching Authority/Written Opinion from International Application No. PCT/US04/23182, Mailing Date: Nov. 3, 2005.

International Searching Authority/Written Opinion from International Application No. PCT/US2005/16689, Mailing Date: Nov. 29, 2005.

Medline Plus, "Doxorubicin" http://www.nlm.nih.gov/medlineplus/druginfo/medmaster/a68221.html accessed Aug. 9, 2005.

Coombes et al., "Lactic acid-stabilised albumin for microsphere formulation and biomedical coatings," Biomaterials, 22:1-8 (2001).

European Search Report for EP Application No. 01987562.4-2114, dated Jul. 20, 2007.

US 5,849,884, 12/1998, Woiszwillo et al. (withdrawn)

\* cited by examiner

PRODUCTION OF MICROSPHERES

RELATED APPLICATIONS

This application is a national stage filing under 35 U.S.C. § 371 of PCT International application PCT/US01/51166, filed Oct. 25, 2001, which was published under PCT Article 21(2) in English, which claims priority under 35 U.S.C. §119 to U.S. Provisional Application Ser. No. 60/244,098, filed Oct. 27, 2000, entitled "Production of Microspheres", the entire contents of which are incorporated herein by reference.

BACKGROUND OF THE INVENTION

This invention relates to a process for preparing protein microspheres having a high protein content. The protein microspheres of this invention are prepared by contacting an aqueous mixture of the protein and a polymer with a surface having a high ratio of surface area to volume. The protein microspheres are suitable for preparing pharmaceutical compositions which can be delivered to a patient, principally by pulmonary, parenteral and oral administration routes. The process can be operated as a continuous process for increased efficiency and productivity.

The preparation and delivery of therapeutic proteins of interest is an area of concentrated research and development activity in the pharmaceutical industry. It is highly desirable to formulate proteins with select release characteristics in the patient with maximum clinical effectiveness. For pulmonary administration, the protein is ideally prepared in the form of discrete microspheres, which are solid or semi-solid particles having a diameter of between 0.5 and 5.0 microns. It is also desirable for the particles to have a protein content as high as possible for maximum therapeutic effectiveness.

Microspheres have been commercially available for biochemical and biotherapeutic applications for many years. For example, antibodies conjugated to beads produce relatively large particles which are specific for a particular ligand. These large antibody-coated particles are used to bind receptors on the surface of a cell for cellular activation, for binding to a solid phase for immunoaffinity purification, and for the delivery of therapeutic agents to a target using tissue or tumor-specific antibodies. The beads can be formed from synthetic polymers or proteins, although synthetic polymers are sometimes preferred due to durability and cost.

Microparticles produced by standard production methods frequently have a wide particle size distribution, lack uniformity, fail to provide adequate release kinetics, and are difficult and expensive to produce. Furthermore, the polymers used to prepare these microspheres are usually soluble in organic solvents, requiring the use of special facilities designed to handle organic solvents. The organic solvents can denature proteins or peptides contained in the microspheres, and may also be toxic when administered to humans or animals.

In addition, the microparticles may be large and tend to form aggregates, requiring a size selection process to remove particles considered to be too large for administration to patients by injection or inhalation. This requires sieving and resulting product loss. Large size particles can also require the use of large gauge needles for injection, often causing discomfort for the patient.

Currently available microspheres are designed to release proteins in an aqueous medium, by incorporating the proteins into a hydrophobic erodible or non-erodible matrix. Many particles exhibit release kinetics based on both erosion and diffusion. In this type of system, an initial burst or rapid release of the drug is observed. This burst effect often results in unwanted side effects in some patients.

U.S. Pat. No. 5,981,719, U.S. Pat. No. 5,849,884 and U.S. Pat. No. 6,090,925, the disclosures of which are incorporated by reference herein in their entirety, describe microparticles formed by combining a macromolecule, such as a protein or peptide, and a polymer in an aqueous solution at a pH near the isoelectric point of the macromolecule. The solution is heated to prepare microparticles having a protein content of greater than 40%. The microparticles thus formed comprise a matrix of substantially homogeneous, intertwined macromolecules and polymers, which permit the aqueous medium to enter and solubilize the components of the microparticle. The microparticles can be designed to exhibit short-term or long-term release kinetics, providing either rapid or sustained release characteristics.

U.S. Pat. No. 6,051,256 relates to processes for preparing powders of biological macromolecules by atomizing liquid solutions of the macromolecules, drying the droplets, and collecting the resulting particles. Biological macromolecules which can be used in this process include insulin and calcitonin.

It will be appreciated that there is a continuing need for a process for preparing and delivering biological agents as microspheres to maximize their effectiveness and minimize the safety concerns for the therapeutic agent.

SUMMARY OF THE INVENTION

The invention provides a process for the production of microspheres of biological molecules of interest. The microspheres are useful as therapeutic or diagnostic agents for treating or diagnosing disease states in a subject in vivo or in vitro. The microspheres are particularly useful as active therapeutic components of inhalers for pulmonary administration to human patients.

The process comprises combining the macromolecule and a polymer in an aqueous solution, contacting a volume of the solution with a surface having a surface area to volume ratio of at least about 6.5 $cm^{-1}$, preferably at least about 14 $cm^{-1}$, and exposing the solution to an energy source for a sufficient period of time to form microspheres. Preferably, the surface is a hydrophobic surface, such as a hydrophobic polymer, or a metal or ceramic material. Particularly preferred surfaces include stainless steel, polypropylene, polystyrene, PTFE and silicone polymers. The microspheres form as a result of the interaction of the solution with the surface, which functions as a site of nucleation for the formation of microspheres.

In one aspect of the invention, the microspheres are substantially spherical in shape, and have mean diameters within the range of from about 0.1 microns and 10.0 microns. Preferably, the mean diameter of the microspheres is within the range of from about 0.5 microns and 5.0 microns, and more preferably within a range of from about 1.0 microns and 2.0 microns.

The macromolecules which are useful in the practice of this invention include both therapeutic and diagnostic agents. Therapeutic agents include antibiotics, hematopoietics, antiinfective agents, antiulcer agents, antiallergic agents, antipyretics, analgesics, antiinflammatory agents, antidementia agents, antiviral agents, antitumoral agents, antidepressants, psychotropic agents, cardiotonics, antiarrythmic agents, vasodilators, antihypertensive agents, antidiabetic agents, anticoagulants, and cholesterol lowering agents. Other examples of suitable macromolecules include proteins, peptides, nucleic acids, carbohydrates, protein conjugates, virus, virus particles, and mixtures thereof. These macromolecules are characterized by the ability to interact with the polymer in the presence of an energy source, such as heat, to form intact, discrete microspheres having a high content of macromolecule. Preferably, the macromolecule comprises at least about 90% by weight of the microspheres, more preferably at least about 95% by weight, and most preferably at least about 99%. In especially preferred embodiments, the microsphere has a sufficiently high protein content to be indistinguishable from the protein standard.

Preferred macromolecules include peptides, such as polypeptides, carbohydrates, such as polysaccharides, proteins, and particularly therapeutic proteins such as insulin, human serum albumin, human growth hormone, parathyroid hormone and calcitonin.

In another aspect, the energy source used to form the microspheres is heat energy. Heat can be applied to the aqueous solution containing the components for the production of the microspheres to heat the solution to a temperature in the range of from about 37° C. to about 95° C. for a time period of about 1 minute to about 24 hours. The aqueous solution can contain water, water-miscible or water soluble solvents, such as ethanol, pyrrolidone, 2-pyrrolidone, DMSO, acetone and the like.

In a further aspect, the polymer incorporated in the aqueous solution is preferably selected from the group consisting of carbohydrate polymers, polyaliphatic alcohols, poly(vinyl) polymers, polyacrylic acids, polyorganic acids, polyamino acids, polyethers, naturally occurring polymers, polyimids, polyesters, polyaldehydes, co-polymers, block co-polymers, terpolymers, surfactants, branched polymers, cyclo-polymers, and mixtures thereof. More preferably, the polymer is dextran, polyethylene glycol, polyvinyl pyrrolidone, co-polymers of polyethylene glycol and polyvinyl pyrrolidone, polyvinyl alcohol, or co-polymers of polyoxyethylene and polyoxypropylene, and mixtures thereof. Most preferably, the polymer is a co-polymer of polyethylene glycol and polyvinyl pyrrolidone, or a co-polymer of polyoxyethylene and polyoxypropylene.

The polymer is a water soluble polymer which is capable of removing water from the macromolecule, or dehydrating the macromolecule. Suitable polymers include, in addition to the specific polymers mentioned above, high molecular weight linear or branched chain polymers which are soluble in water, or in a water miscible solvent, or both. Typical water soluble polymers which are useful in this invention are described in pending, commonly assigned U.S. patent application Ser. No. 09/420,361, filed Oct. 18, 1999, the disclosure of which is incorporated herein in its entirety.

In a still further aspect, an apparatus which can be used to prepare the microspheres of the present invention comprises a reactor having an internal surface to volume ratio of 6.5 $cm^{-1}$, and means for heating the aqueous solution. The reactor contains an aqueous solution of a macromolecule and a polymer. The internal surface contacts the aqueous solution and increases the internal surface area of the reactor. Preferably, the internal surface is provided by a bed of inert, solid material, such as a bed of pellets, balls, plates, and the like, Alternatively, the internal surfaces can include tubes through which the solution passes.

In order to prepare the microspheres of the present invention, the surface area of the internal surface should be sufficient to provide a surface area to volume ratio of at least about 6.5 $cm^{-1}$, and preferably at least about 14 $cm^{-1}$. Preferably, the surfaces are formed from a hydrophobic material, particularly hydrophobic polymers such as polypropylene, polystyrene, PTFE or silicone polymers. Alternatively, the surfaces can be formed from metals, ceramics or glass. A preferred metal is stainless steel. The surface functions as a site of nucleation for the formation of microspheres.

The apparatus for preparing the microspheres of this invention can be operated in a batch or continuous mode. Continuous mode operation is typically more efficient and cost effective than batch mode.

In yet another aspect, the invention includes devices and methods for delivering the microspheres to a subject, and particularly a human patient in need of medical treatment. Suitable delivery routes include parenteral, such as i.m., i.v. and s.c., and non-parenteral, such as oral, buccal, intrathecal, nasal, pulmonary, transdermal, transmucosal, and the like. Delivery devices include syringes, both needleless and needle containing, and inhalers.

The syringe can contain a single dose of the microspheres for treating a condition that is treatable by the sustained release of the macromolecule in vivo. The number of microspheres present in the single dose is dependent on the type and activity of the macromolecule. Preferably, the single dose is selected to achieve sustained release over a period of time which has been optimized for treating the particular medical condition.

An inhaler device can be utilized when it is desired to deliver a therapeutic dose of protein microspheres to the lung of a subject. The protein microspheres are prepared by contacting an aqueous solution of the protein and a polymer with a surface, and heating the solution to form the microspheres. The protein is preferably a therapeutic protein, such as insulin, human growth hormone, calcitonin or parathyroid hormone, and the protein content of the microspheres is preferably at least about 90% or more, more preferably 95% or more, and most preferably at least about 99% or more. For pulmonary administration, the microspheres are ideally sized to have a mean diameter in the range of from about 0.5 microns to 5.0 microns, and preferably between 1 and 2 microns.

The inhaler can be used to treat any medical condition in which the protein can be administered by inhalation therapy. Typical inhaler devices include dry powder inhalers, metered dose inhalers, nebulizers and electrostatic delivery devices. Typical applications of the delivery apparatus of this invention include the deep lung delivery of insulin and similar proteins.

The microspheres of this invention can be prepared without the need for spray drying or milling processes. These microspheres are homogenous in size and shape, and reproducible between different batches. The protein microspheres have been found to be unexpectedly stable and to form superior suspensions in the presence of propellants, both freon-based and freon substitutes, that are commonly used in inhalers for pulmonary delivery. It is believed that this increased stability may be due to the fact that the microspheres of this invention are dehydrated as a result of the interaction of the polymer and the macromolecule, and have increased stability in the presence of inhaler propellants.

Although pulmonary delivery is preferred, the microspheres of this invention can be delivered orally, intranasally, intravenously intramuscularly, subcutaneously, and by other delivery methods suitable for the delivery of therapeutic molecules.

These and other aspects of the invention will be described in greater detail herein. All technical and scientific terms have the meaning ascribed herein, or if not so ascribed, as commonly understood by one of ordinary skill in this art.

DETAILED DESCRIPTION OF THE INVENTION

Figure 1:
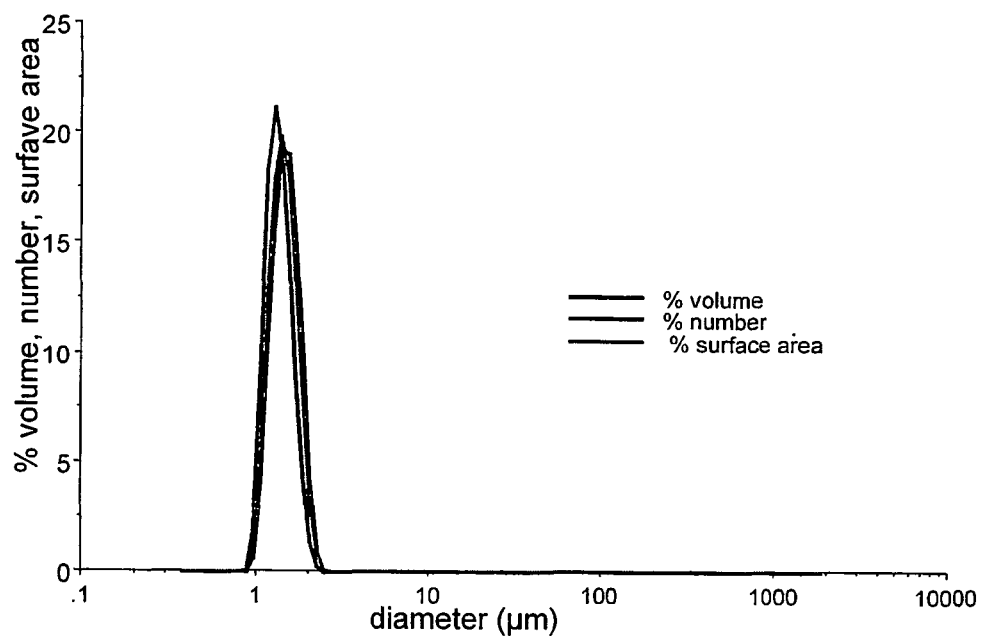
FIG. 1 is a graph showing the number of particles, surface area average and volume average for microspheres of the invention as a function of the diameter of the particles. The microspheres depicted in the figure are prepared from polyethylene glycol, polyvinyl pyrrolidone and insulin.

A process for preparing microspheres having therapeutic and diagnostic applications is described herein. The process involves combining a macromolecule and a polymer in an aqueous solution, and exposing the aqueous solution to an energy source. According to the process of this invention, a volume of the aqueous solution contacts a surface under conditions wherein the surface area to volume ratio of at least about 6.5 cm$^{-1}$, and preferably at least about 14 cm$^{-1}$. The surface serves as a site of nucleation promoting the formation of the microspheres.

Therapeutic and diagnostic applications of the microspheres include drug delivery, vaccination, gene therapy, and in vivo tissue or tumor imaging. Routes of administration include oral or parenteral administration; mucosal administration; ophthalmic administration; intravenous, subcutaneous, intra articular, or intramuscular injection; inhalation administration; and topical administration.

The term "microspheres", as used herein, denotes particles substantially spherical in shape having dimensions generally of between about 0.1 microns and 10.0 microns in diameter. The microspheres typically exhibit a narrow size distribution, and are formed as discrete particles.

An "aqueous solution", as that term is used herein, includes solutions of water alone, or water mixed with one or more water-miscible solvents, such as ethanol, DMSO, acetone and methyl pyrrolidone, 2-pyrrolidone.

The microspheres are produced by mixing macromolecules in an aqueous mixture with a water soluble polymer or mixture of polymers, thereafter contacting the solution with an energy source, preferably heat, under conditions sufficient to form the microspheres. The solution is preferably an aqueous solution. Either the macromolecule solution is added to the polymer, or the polymer solution is added to the macromolecule solution, to cause removal of water from, or dehydration of, the macromolecule. This process is also referred to by those skilled in the art as volume exclusion.

The macromolecule and polymer solution is then exposed to an energy source, such as heat, radiation, including microwave radiation, or ionization, alone or in combination with sonication, vortexing, mixing or stirring, for a predetermined length of time to form and stabilize the microspheres. The resulting microspheres are then separated from any unincorporated components present in the solution by physical separation methods well known to those skilled in the art, and may then be washed or exposed to other drug-containing solutions for binding of additional drugs to the microspheres.

The length of incubation time is dependent upon the respective concentrations of polymer and macromolecule and the level of energy of the energy source. Microsphere stabilization can begin to occur immediately upon exposure to the energy source. Preferably, the macromolecule and polymer mixture is heated at a temperature greater than room temperature for between approximately 1 minute and 24 hours. Most preferably, the polymer and macromolecules are heated for 30 minutes or less at a temperature between approximately 37° C. and 95° C.

The formation of the microspheres according to this invention requires a site of nulceation which is commonly the vessel or container for the macromolecule and polymer aqueous solution. This is accomplished by combining the macromolecule and polymer under conditions sufficient to provide a surface area to volume ratio of at least about 6.5 cm$^{-1}$, and preferably at least about 14 cm$^{-1}$. The surfaces can be formed from a hydrophobic material, such as a hydrophobic polymer, such as polypropylene. Alternatively, the surface can be formed from a metal, a ceramic or glass.

The vessel may inherently have a high surface area to volume ratio, as in the case of a tubular reactor, so that no adjustment with respect to this ratio is required. Alternatively, the surface area to volume ratio in a vessel can be increased by adding materials to the vessel to reduce the internal volume relative to the surface area. This can be accomplished by using a bed of particles, plates, or beads, for example, in the reactor.

The macromolecule component of the microsphere is any molecule having a tertiary and quaternary structure or capable of having a tertiary and quaternary structure. Most preferably, the macromolecule is a biomolecule such as a protein, including enzymes and recombinant proteins, peptides, carbohydrates, polysaccharides, carbohydrate- or polysaccharide-protein conjugates, nucleic acids, virus, virus particles, conjugates of small molecules (such as a hapten) and proteins, or mixtures thereof. An organic or inorganic natural or synthetic pharmaceutical compound or drug may be incorporated into the microspheres by attaching the drug to a macromolecule, such as a protein, and then forming the microspheres from the macromolecule-drug complex or conjugate. It will be understood by those skilled in the art that a compound incapable of having a tertiary and quaternary structure can be formed into a microsphere by incorporation or coupling of the compound into a carrier molecule that has a tertiary and quaternary structure. It will be further understood by those skilled in the art that the macromolecule can be a portion of a molecule such as, for example, a peptide, a single-stranded segment of a double-stranded nucleic acid molecule, or a virus particle, having a tertiary and quaternary structure. It will also be understood that the term "macromolecule" includes a plurality of macromolecules and includes combinations of different macromolecules such as a combination of a pharmaceutical compound and an affinity molecule for targeting the pharmaceutical compound to a tissue, organ or tumor requiring treatment. It will be further understood that an affinity molecule can be either the receptor portion or the ligand portion of a receptor-ligand interaction. Examples of ligands that interact with other biomolecules include viruses, bacteria, polysaccharides, or toxins that act as antigens to generate an immune response when administered to an animal and cause the production of antibodies.

Suitable compounds or macromolecules include, but are not limited to, betaxolol™, diclofenac™, doxorubicin, rifampin™, leuprolide acetate, luteinizing hormone releasing hormone (LHRH), (D-Tryp6)-LHRH, nafarelin acetate, insulin, sodium insulin, zinc insulin, protamine, lysozyme, alpha-lactalbumin, basic fibroblast growth factor (bFGF), beta-lactoglobulin, trypsin, calcitonin, parathyroid hormone, carbonic anhydrase, ovalbumin, bovine serum albumin (BSA), human serum albumin (HSA), phosphorylase b, alkaline phosphatase, beta-galactosidase, IgG, fibrinogen, poly-L-lysine, IgM, DNA, desmopressin acetate, growth hormone releasing factor (GHRF), somatostatin, antide, Factor VIII, G-CSF/GM-CSF, human growth hormone (hGH), beta interferon, antithrombin III, alpha interferon, alpha interferon $2b$.

The incubation conditions are typically optimized to incorporate at least about 90%, preferably at least about 95%, and most preferably at least about 99%, of the macromolecule in the reaction mixture by adjusting the pH, temperature, concentration of macromolecule, or duration of reaction or incubation. In general, less energy is required to form microspheres at higher concentrations of macromolecule.

Microspheres composed of nucleic acids are preferably prepared by first mixing the nucleic acid either with a protein, such as bovine serum albumin, or, because nucleic acids are anions, by the addition of a cation, such as polylysine, which aids greatly in the formation of microspheres.

As mentioned above, a small molecule or compound incapable of having a tertiary and quaternary structure, such as a peptide or pharmaceutical compound, can be formed into a microsphere by incorporation or coupling of the compound into a carrier molecule that has a tertiary and quaternary structure. This may be achieved in several ways. For example, microspheres may be formed as described herein using a macromolecule having a tertiary and quaternary structure, such as a protein, and then the small molecule or compound is bound inside and/or on the surface of the microsphere. Alternatively, the small molecule or compound is bound to the macromolecule having a tertiary and quaternary structure using hydrophobic or ionic interactions, and then microspheres are formed from the macromolecule-small molecule complex using the method described herein. A third way to make microspheres from small molecules is to prepare microspheres using a macromolecule having a tertiary and quaternary structure in such a way that the microsphere has a net charge and then add a small molecule or compound having an opposite net charge so that the small molecule is physically attracted to and remains attached to the microsphere, but can be released over time under the appropriate conditions. Alternatively, different types of non-covalent interactions such as hydrophobic or affinity interactions may be used to allow attachment and subsequent release of small molecules.

When preparing microspheres containing a protein, a protein stabilizer such as glycerol, fatty acids, sugars such as sucrose, ions such as zinc, sodium chloride, or any other protein stabilizers known to those skilled in the art may be added prior to the addition of the polymers during microsphere formation to minimize protein denaturation.

Molecules, distinct from the macromolecules of which the microspheres are composed, may be attached to the outer surface of the microspheres by methods known to those skilled in the art to "coat" or "decorate" the microspheres. The ability to attach molecules to the outer surface of the microsphere is due to the high concentration of macromolecule in the microsphere. These molecules are attached for purposes such as to facilitate targeting, enhance receptor mediation, and provide escape from endocytosis or destruction. For example, biomolecules such as phospholipids may be attached to the surface of the microsphere to prevent endocytosis by endosomes; receptors, antibodies or hormones may be attached to the surface to promote or facilitate targeting of the microsphere to the desired organ, tissue or cells of the body; and polysaccharides, such as glucans, or other polymers, such as polyvinyl pyrrolidone and PEG, may be attached to the outer surface of the microsphere to enhance or to avoid uptake by macrophages.

In addition, one or more cleavable, erodilbe or soluble molecules may be attached to the outer surface of or within the microspheres. The cleavable molecules are designed so that the microspheres are first targeted to a predetermined site under appropriate biological conditions and then, upon exposure to a change in the biological conditions, such as a pH change, the molecules are cleaved causing release of the microsphere from the target site. In this way, microspheres are attached to or talen up by cells due to the presence of the molecules attached to the surface of the microspheres. When the molecule is cleaved, the microspheres remain in the desired location, such as within the cytoplasm or nucleus of a cell, and are free to release the macromolecules of which the microspheres are composed. This is particularly useful for drug delivery, wherein the microspheres contain a drug that is targeted to a specific site requiring treatment, and the drug can be slowly released at that site. The preferred site of cleavage is a diester bond.

The microspheres may also be coated with one or more stabilizing substances, which may be particularly useful for long term depoting with parenteral administration or for oral delivery by allowing passage of the microspheres through the stomach or gut without dissolution. For example, microspheres intended for oral delivery may be stabilized with a coating of a substance such as mucin, a secretion containing mucopolysaccharides produced by the goblet cells of the intestine, the submaxillary glands, and other mucous glandular cells.

Additionally, the microspheres can be non-covalently coated with compounds such as fatty acids or lipids. The coating may be applied to the microspheres by immersion in the solubilized coating substance, spraying the microspheres with the substance or other methods well known to those skilled in the art.

In certain of the preferred embodiments, the microspheres of the invention include a protein and at least one water soluble polymer. As discussed above, the microspheres are formed by contacting the protein and at least one water soluble polymer under aqueous conditions, and the microspheres are then formed and stabilized by exposing the microspheres to an energy source, preferably heat, under conditions (e.g., concentration, temperature) which result in microspheres which are resistant to physical and chemical treatments such as sonication and caustic solutions.

In general, the microspheres of the invention are formed by mixing the protein together with at least one water soluble polymer under suitable conditions which, preferably, permit the water soluble polymer to remove water from ("dehydrate") the protein within specified or preferred ratios (wt/wt) of protein to water soluble polymer (e.g., ratios range from about 1 protein: 1 polymer to about 1 protein: 1000 polymer). The preferred ratio of protein to water soluble polymer in the microsphere formation reaction is in the range from about 1 protein: 5 polymer to about 1 protein: 30 polymer. As noted above, a "water soluble polymer" of the invention refers to a polymer or mixture of polymers which, preferably, are capable of interacting with the macromolecule (e.g., protein or other molecule) to cause volume exclusion.

Suitable water soluble polymers include soluble linear or branched polymers, preferably those having a high molecular weight. Polymers can be highly water soluble, moderately-water soluble, or slightly water soluble (greater than 2% wt/vol water soluble). The preferred water soluble polymers are water soluble or soluble in a water miscible solvent. The water soluble polymers may be solubilized by first being dissolved in water, an aqueous buffered solution, or a water miscible solvent and then combining the polymer solution with an aqueous solvent. In one embodiment, the water soluble polymer is a carbohydrate-based polymer. The preferred polymer is polyvinylpyrrolidone, polyethylene glycol, dextran, polyoxyethylene-polyoxypropylene copolymer, polyvinyl alcohol, starch, hetastarch, or mixtures thereof, the characteristics of which are described in more detail below. The polymer or polymer mixture may be prepared in accordance with the methods set forth in U.S. Pat. No. 5,525,519 to James E. Woiszwillo, or PCT Patent Application No. US93-00073 (International Publication No. WO 93/14110), filed Jan. 7, 1993 and published on Jul. 22, 1993 by James E. Woiszwillo, both of which are incorporated herein by reference), in which the polymer is dissolved in water or an aqueous solution, such as a buffer, in a concentration between approximately 1 and 50 g/100 ml depending on the molecular weight of the polymer. The preferred total polymer concentration in the polymer solution is between 10% and 80%, expressed as weight/volume percent. The preferred concentration of each polymer in the polymer solution is between 5% and 50%.

Polyoxyethylene-polyoxypropylene copolymer, also known as poloxamer, is sold by BASF (Parsippany, N.J.) and is available in a variety of forms with different relative percentages of polyoxyethylene and polyoxypropylene within the copolymer.

PVP is a non-ionogenic, hydrophilic polymer having a mean molecular weight ranging from approximately 10,000 to 700,000 and the chemical formula $(C_6H_9NO)[n]$. PVP is also known as poly[1-(2-oxo-1-pyrrolidinyl)ethylene], Povidone™, Polyvidone™, RP 143™, Kollidon™, Peregal ST™, Periston™, Plasdone™, Plasmosan™, Protagent™, Subtosan™, and Vinisil™. PVP is non-toxic, highly hygroscopic and readily dissolves in water or organic solvents.

Polyethylene glycol (PEG), also known as poly(oxyethylene) glycol, is a condensation polymer of ethylene oxide and water having the general chemical formula $HO(CH_2CH_2O)[n]H$.

Dextran is a term applied to polysaccharides produced by bacteria growing on a sucrose substrate. Native dextrans produced by bacteria such as Leuconostoc mesenteroides and *Lactobacteria dextranicum* usually have a high molecular weight. Dextrans are routinely available and are used in injectable form as plasma expanders in humans.

Polyvinyl alcohol (PVA) is a polymer prepared from polyvinyl acetates by replacement of the acetate groups with hydroxyl groups and has the formula $(CH_2CHOH)[n]$. Most polyvinyl alcohols are soluble in water.

PEG, dextran, PVA and PVP are commercially available from chemical suppliers such as the Sigma Chemical Company (St. Louis, Mo.).

Preferably, the polymer is a polymer mixture containing an aqueous solution of PVP having a molecular weight between 10,000 and 360,000, most preferably 40,000, and PEG having a molecular weight between 200 and 35,000. PVP having a molecular weight of 40,000 and PEG having a molecular weight of 3500 is preferred. Preferably, the PVP is dissolved in an acetate buffer and PEG is added to the aqueous PVP solution. The concentration of each polymer is preferably between 1 and 40 g/100 ml depending of the molecular weight of each polymer. Equal concentrations of PVP and PEG generally provide the most favorable polymer mixture for the formation of microspheres.

An alternative preferred polymer is a dextran, having a molecular weight from approximately 3000 to 500,000 daltons.

The volume of polymer added to the macromolecule varies depending on the size, quantity and concentration of the macromolecule. Preferably, two volumes of the polymer mixture at a 5-50% total polymer concentration are added to one volume of a solution containing the macromolecule, typically at a concentration of 10 mg/ml. The polymer is present in a liquid phase during the reaction with macromolecule.

Applicants have discovered that contacting a volume of the aqueous solution with a surface having a surface area to volume ratio of at least about 6.5 $cm^{-1}$, preferably at least about 14 $cm^{-1}$, results in the formation spherically shaped microspheres rather than aggregates and other amorphous forms of particles. Preferably, the surface is a hydrophobic surface, such as a hydrophobic polymer, or a metal or ceramic material. Particularly preferred surfaces include stainless steel, polypropylene, polystyrene, PTFE and silicone polymers. The surfaces can take the form of tubes, or a bed of pellets, balls, plates, etc. The microspheres are believed to form as a result of the interaction of the solution with the surface, which functions as a site of nucleation for the formation of microspheres.

The process can be operated in a batch or continuous mode. Continuous mode operation is typically more efficient and cost effective than batch mode.

The preferred energy source is heat. However, it will be understood by those skilled in the art that other energy sources include heat, radiation, and ionization, alone or in combination with sonication, vortexing, mixing or stirring. Microsphere formation can occur immediately upon exposure to the energy source or may require an extended exposure to the energy source depending on the characteristics of the components and conditions. Preferably, the macromolecule-polymer solution mixture, is incubated in a water bath at a temperature greater than or equal to 37° C. and less than or equal to 95° C. for between approximately 1 minute and 24 hours. Most preferably, the mixture is incubated for 5-30 minutes at a temperature between 50° C. and 90° C. The maximum incubation temperature is determined by the characteristics of the macromolecule and the ultimate function of the microsphere.

The formed microspheres are separated from the non-incorporated components of the incubation mixture by conventional separation methods well known to those skilled in the art. Preferably, the incubation mixture is centrifuged so that the microspheres sediment settles to the bottom of the centrifuge tube and the non-incorporated components remain in the supernatant, which is then removed by decanting. Alternatively, a suspension containing formed microspheres is filtered so that the microspheres are retained on the filter and the non-incorporated components pass through the filter.

Further purification of the microspheres is achieved by washing in an appropriate volume of a washing solution. The preferred washing solution water, or a water-miscible solvent capable of removing the water soluble polymers. Repeated washings can be utilized as necessary and the microspheres separated from the wash solution as described above.

As mentioned above, the characteristics of the microspheres can be altered by manipulating the incubation conditions. For example, the release kinetics of the microspheres may be retarded by increasing the reaction temperature or extending the length of reaction time during microsphere formation. Release kinetics are also manipulated by choosing different polymers, different concentrations of polymers, or different ratios of polymers used in the formation of the microspheres.

Microsphere size, shape and release kinetics can also be controlled by adjusting the microsphere formation conditions. For example, microsphere formation conditions can be optimized to produce smaller or larger microsplieres, or the overall incubation time or incubation temperature can be increased, resulting in microspheres which have prolonged release kinetics.

According to yet another aspect of the invention, a pharmaceutical composition of matter and method for producing same are provided. The composition includes a container containing a single dose of microspheres containing an active agent for treating a condition that is treatable by the sustained release of an active agent from the microspheres. The number of microspheres in the single dose is dependent upon the amount of active agent present in each microsphere and the period of time over which sustained release is desired. Preferably, the single dose is selected to achieve the sustained release of the active agent over a period of about 1 to about 180 days with the desired release profile.

According to another aspect of the invention, a syringe-containing composition is provided. The composition includes a syringe containing a single dose of microspheres containing an active agent for treating a condition that is treatable by the sustained release of the active agent from the microspheres; and a needle attached to the syringe, wherein the needle has a bore size that is from 14 to 30 gauge.

The preferred microspheres of the invention can also be prepared to have dimensions which permit the delivery of microspheres using a needleless syringe, thereby eliminating the disposal problems inherent with needles which must be disposed as a biohazard waste product. Thus, according to a particularly preferred aspect of the invention, a needleless syringe containing one or more doses of microspheres containing an active agent for treating a condition is provided.

The microspheres can also be prepared to have qualities suitable to be delivered by other parenteral and non-parenteral routes such as oral, buccal, intrathecal, nasal, pulmonary, transdermal, transniucosal and the like.

An inhaler device can be utilized for pulmonary delivery of a therapeutic dose of protein microspheres to the lung of a subject. For pulmonary administration, the microspheres are ideally sized to have a mean diameter in the range of from about 0.5 microns to 5.0 microns, and preferably between 1 and 2 microns.

The inhaler can be used to treat any medical condition in which the protein can be administered by inhalation therapy. Typical inhaler devices include dry powder inhalers, metered dose inhalers, nebulizers and electrostatic delivery devices. Typical applications of the delivery device includes the deep lung delivery of insulin and similar proteins.

The protein microspheres have been found to be unexpectedly stable in the presence of propellants, both freon-based and freon substitutes, commonly used in inhalers for pulmonary delivery. Without wishing to be bound by any theory or mechanism of operability, it is believed that this increased stability may be due to the fact that the microspheres of this invention are dehydrated as a result of the interaction of the polymer and the macromolecule. This allows the microspheres to remain intact for prolonged periods of time in the presence of inhaler propellants.

When used therapeutically, the microspheres of the invention are administered in therapeutically effective amounts. In general, a therapeutically effective amount means that amount of macromolecule necessary to affect a therapeutic response or to delay the onset of, inhibit the progression of, or halt altogether the particular condition being treated. Generally, a therapeutically effective amount will vary with the subject's age, condition, and sex, as well as the nature and extent of the disease in the subject, all of which can be determined by one of ordinary skill in the art. The dosage may be adjusted by the individual physician or veterinarian, particularly in the event of any complication. A therapeutically effective amount of active agent typically varies from 0.01 mg/kg to about 1000 mg/kg, preferably from about 0.1 mg/kg to about 200 mg/kg, and most preferably from about 0.2 mg//kg to about 20 mg/kg, in one or more dose administrations daily, for one or more days, weekly, monthly, every two or three months, and so forth.

The microspheres may be administered alone or in combination with other drug therapies as part of a pharmaceutical composition. Such a pharmaceutical composition may include the microspheres in combination with any standard physiologically and/or pharmaceutically acceptable carriers which are known in the art. The compositions should be sterile and contain a therapeutically effective amount of the microspheres in a unit of weight or volume suitable for administration to a patient. The term "pharmaceutically-acceptable carrier" as used herein means one or more compatible solid or liquid fillers, diluents or encapsulating substances which are suitable for administration to a human or other animal. The term "carrier" denotes an organic or inorganic ingredient, natural or synthetic, with which the active ingredient is combined to facilitate the application.

"Pharmaceutically acceptable" further means a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, desiccants, bulling agents, propellants, acidifying agents, coating agents, solubilizers, and other materials which are well known in the art. Carrier formulations suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular drug selected, the severity of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion.

The pharmaceutical compositions may conveniently be presented in unit dosage form and may be prepared by any of the methods well-known in the art of pharmacy. All methods include the step of bringing the microspheres into association with a carrier which constitutes one or more accessory ingredients. In general, the compositions are prepared by uniformly and intimately bringing the microspheres into association with a liquid carrier, a finely divided solid carrier, or both, and then, if necessary, shaping the product.

Preparations for parenteral administration include sterile aqueous or non-aqueous solutions, suspensions, and emulsions. Additional examples of solvents include propylene glycol, polyethylene glycol, vegetable oils such as olive oil, and injectable organic esters such as ethyl oleate. Aqueous carriers include water, salts and buffer solutions such as saline and buffered media, alcoholic/aqueous solutions and emulsions or suspensions. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. In general, the microspheres can be administered to the subject (any mammalian recipient) using the same modes of administration that currently are used for microparticle therapy in humans.

The microspheres are useful as therapeutic agents and may enable the use of alternative routes of administration when the microspheres include a therapeutic drug and are administered to a patient for slow release or targeted delivery of the drug to the site requiring therapy. The microspheres are also useful as therapeutic or prophylactic agents when the microspheres include a macromolecule that is itself a therapeutic or prophylactic agent, such as an enzyme or immunoglobulin. The slow release of such therapeutic agents is particularly useful for therapeutic proteins or peptides having short half-lives that must be administered by injection.

The microspheres are useful for therapy or prophylaxis when the macromolecule is a therapeutic agent or a pharmaceutical compound that is delivered to a patient and slowly released from the microspheres over time. These microspheres are particularly useful for slow release of drugs with short biological half-lives, such as proteins or peptides. If the pharmaceutical compound cannot be formed into a particle, then it is completed to a carrier, such as albumin, and the carrier-pharmaceutical compound complex is formed into a microsphere. The microsphere can either provide for the slow release of the agent throughout the body or the microsphere can include an affinity molecule specific for a target tissue, or tumor, and be injected into a patient for targeted slow release of the therapeutic agent, such as an antitumor, antiviral, antibacterial, antiparasitic, or antiarthritic agent, cytokine, hormone, or insulin directly to the site requiring therapy.

The following examples are illustrative of certain embodiments of the invention, and are intended to further describe the present invention, without limiting it thereby. Various modifications can be made to these embodiments without departing from the spirit or scope of the invention.

EXAMPLE 1

Preparation of Insulin Microspheres in Vessels of Various Sizes

Insulin microspheres are prepared according to the methods described in U.S. Pat. No. 5,981,719, the disclosure of which is incorporated herein by reference in its entirety. The microspheres are formed by incorporating aqueous solutions of insulin, polyethylene glycol and polyvinyl pyrrolidone in centrifuge tubes, and heating the solution to temperatures ranging from 37° C. up to 95° C. for a time period of about 30 minutes.

Four (4) different size centrifuge tubes are used as follows: 1.5 mL, 15 mL, 50 mL, and 100 mL. Microspheres of defined particle size and spherical shape are formed in the 1.5 mL tubes, but only amorphous precipitates rather than microspheres are formed in the 15 mL, 50 mL and 100 mL tubes. Attempts to form microspheres in the 15 mL, 50 mL and 100 mL tubes using changes in heating conditions, pH, protein concentration, polymer concentration or type, heating time, or stirring condition alteration are not successful, and microspheres cannot be reproducibly formed in the larger tubes.

The surface area to volume ratio of the tubes is calculated. The 1.5 mL tube has a surface area to volume ratio of about 14 $cm^{-1}$; the 15 mL tube has a surface area to volume ratio of about 6.5 $cm^{-1}$; and the 50 mL tube has a surface area to volume ratio of about 3.5 $cm^{-1}$.

EXAMPLE 2

Preparation of Insulin Microspheres in Vessel Having a Packed Bed

The production of insulin microspheres is undertaken in a container having an increased surface area relative to the volume of the insulin/polymer solution. In order to demonstrate the effects of a relatively high surface area, a polypropylene 50 mL centrifuge tube is cut into plastic shards approximately 5 cm in length and 1 cm in width. These plastic shards are then placed in a 15 mL polypropylene centrifuge tube. 3.35 mL of a 10 mg/mL insulin solution in deionized water adjusted to pH 3 with 1 N HCl is added to the centrifuge tube. 6.66 mL of 12.5% (wt/vol) polyethylene glycol (PEG, MW-3350 daltons), and 12.5% (wt/vol) polyvinyl pyrrolidone (PVP, MW-40,000) in 100 mM sodium acetate buffer, pH 5.6 is added to the 15 mL centrifuge tube. A control experiment is also conducted using a similar 15 mL polypropylene tube containing no polypropylene shards with the same quantity of insulin and PEG/PVP solution as described above.

The solutions are heated in a 91° C. water bath without shaking for 15 minutes. After this time, the tubes are centrifuged at 3200 rpm for 20 minutes. The tubes are removed from the centrifuge, and the supernatant is discarded. Five (5) mL of deionized water is added to the pellet, and the tube is vortexed to resuspend the pellet. The tube is then centrifuged again at 3200 rpm for 20 minutes. This wash step is repeated.

The microspheres are then subjected to particle size analysis by a Coulter laser light diffraction particle size analyzer.

The data in FIG. 1 shows that the particle size of greater than 95% of the insulin microspheres prepared according to the process of this invention is 1.5 microns by number average, surface area average and volume average statistics. These close agreements in particle size are indicative of a very homogeneous microsphere population with no evidence of aggregate formation.

Scanning electron micrographs (SEMs) of 1-2 micron insulin microspheres are prepared by lyophilizing the insulin microspheres, and sputter coating them with gold. The microspheres are then observed under a scanning electron microscope.

Figure 2:
FIG. 2 is a scanning electron micrograph (SEM) of insulin aggregates prepared by a procedure other than the process of this invention. An amorphous mass of lyophilized insulin is shown.
Figure 3:
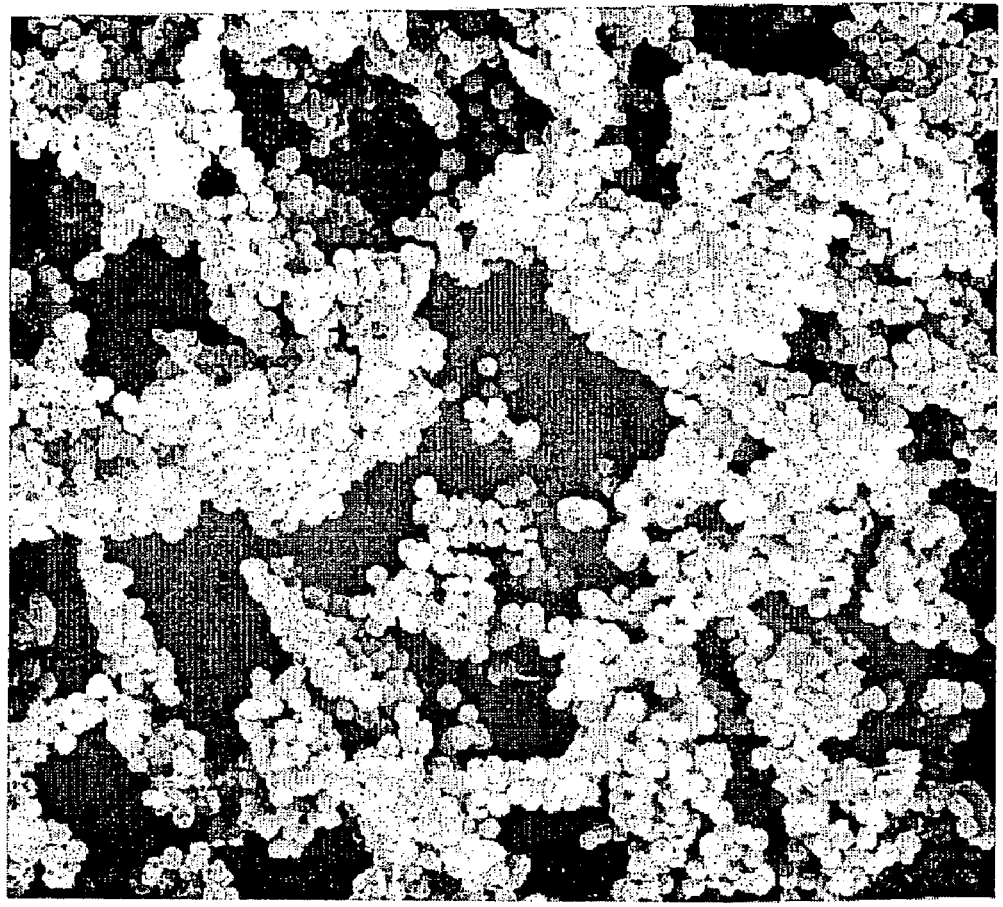
FIG. 3 is a scanning electron micrograph of 1 to 2 micron insulin microspheres prepared using polypropylene shards according to the process of this invention.

An SEM of 1-2 micron insulin microspheres prepared according to the process of this invention is shown in FIG. 3, which shows evidence that discrete, non-aggregated microspheres are formed. As a control, FIG. 2 shows a sample of lyophilized insulin not subjected to the microsphere fabrication conditions described herein. FIG. 2 shows a large amorphous mass of lyophilized insulin, with no evidence of microsphere formation.

Figure 4:
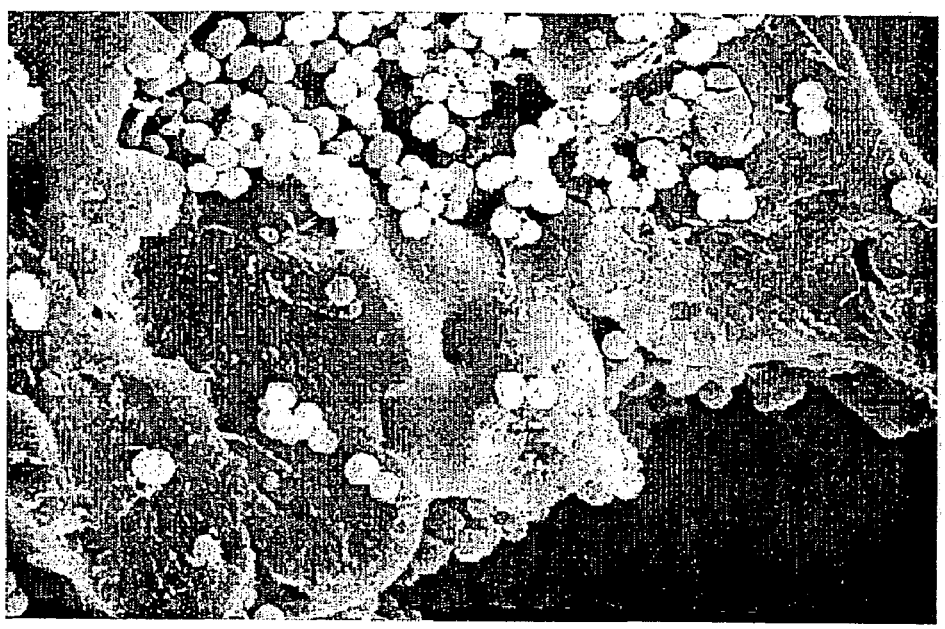
FIG. 4 is a scanning electron micrograph showing insulin aggregates prepared without the use of the polypropylene shards of this invention. As shown in the micrograph, the vast majority of the mass constitutes aggregated material with very few actual microspheres.

A study conducted without the addition of plastic shards at the same 10 mL scale yields aggregates seen in FIG. 4. FIG. 4 shows a mass of aggregated material with very few microspheres present.

For tube volumes greater than 1.5 mL, particle size analysis indicated that without the presence of increased surface area effected by the presence of the PP plastic shards, insulin microsphere aggregates and large particle formation were commonly observed. See FIG. 5.

Figure 5A:
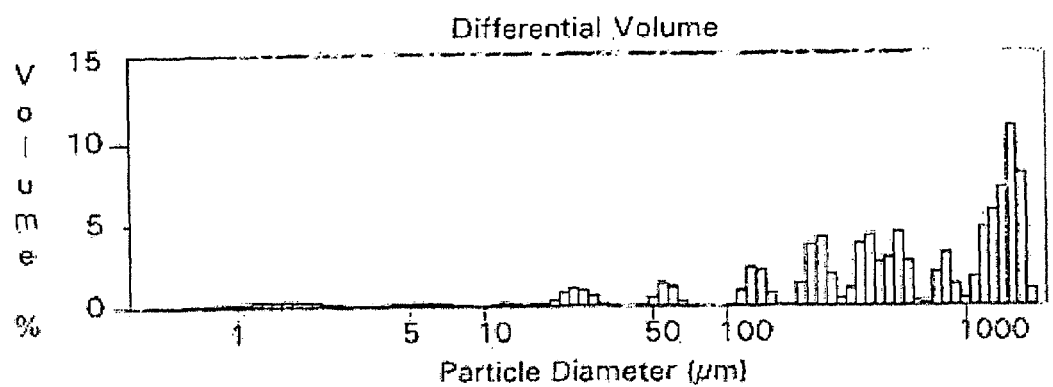
FIGS. 5A, 5B and 5C are graphical representations showing the differential volume, differential number and differential surface area, respectively, of microspheres prepared without the use of polypropylene shards, as a function of the particle diameter.
Figure 5B:
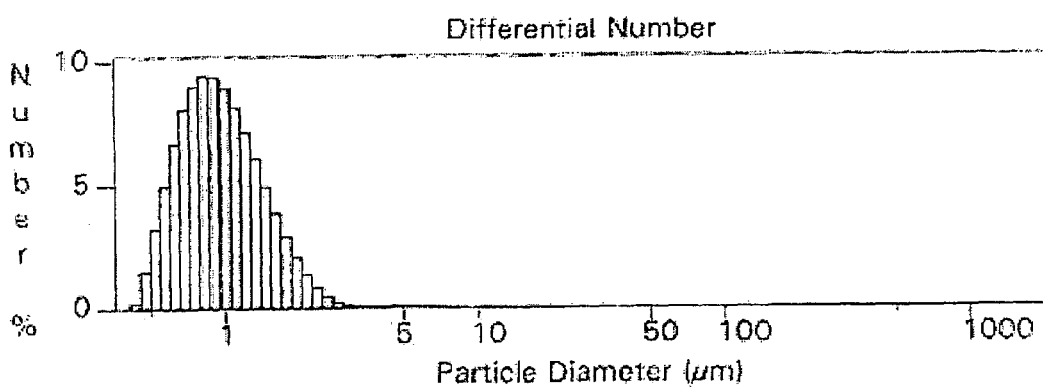
Figure 5C:
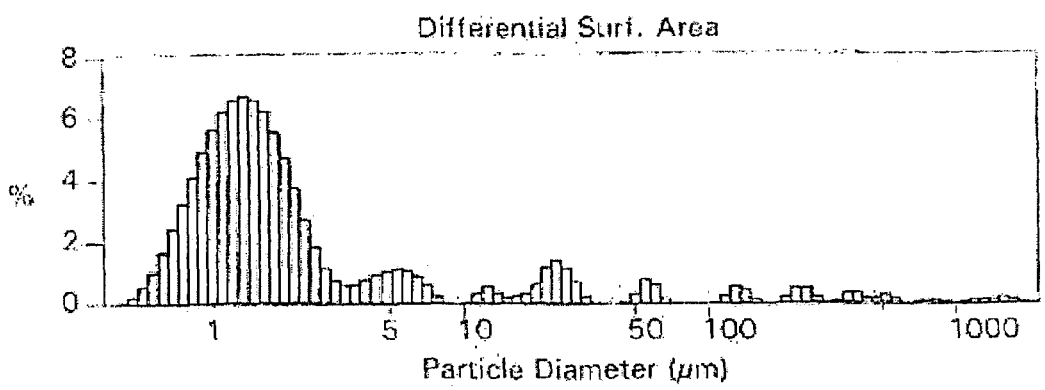

FIG. 5 is a particle size analysis of microspheres prepared by a process outside of the scope of the present invention, such as in large tubes which do not have their internal surface area increased by the presence of polypropylene shards. FIG. 5 shows that the number average particle size is 1.05 microns. This indicates that there are a lot of small particles. However, the surface area and volume average particle size statistics are 31.0 microns and 783.2 microns, respectively. This indicates that without adequate surface area in the fabrication tubes, large insulin aggregates also form. The particle size analysis in FIG. 5 can be contrasted with FIG. 1 which shows no evidence of insulin aggregate formation.

EXAMPLE 3

Continuous Production of Protein Microspheres

An apparatus is assembled for the production of microspheres of uniform small size without aggregates. The apparatus contains a pump for pumping insulin/PEG/PVP solutions through narrow bore plastic tubing made from polypropylene or other similar materials at elevated temperatures. In this manner, continuous flow-through methods can be used to continuously produce microspheres in a controlled and reproducible fashion. The use of relatively small bore tubing ($\frac{1}{32}$ to $\frac{1}{8}$ inch inner diameter), insures a high surface area to volume ratio, and submersing the tubing in a controlled temperature water bath permits the temperature to be controlled until the formation of the microspheres is complete.

The following materials are used in this example:
Teflon (TFE $\frac{1}{32}$" inner diameter flexible tubing)
Insulin (Calbiochem cat #40769)
25% PEG/PVP pH 5.6 in 100 mM NaOAc buffer water bath at 90° C. (American Scientific Products)

36.5 mg of insulin is weighed out and suspended in 3 mL of deionized water. 30 µL of 1 N HCl is added to dissolve the insulin. The final volume of the solution is QS'ed to 3.65 mL with deionized water. 7.3 mL of PEG/PVP solution is then added to the insulin solution which is then vortexed. This yields a homogeneous suspension of insulin and PEG/PVP.

The tubing is connected through a BioRad peristaltic pump running at a speed of 0.4 mL/min. The tubing is submerged into the 90° C. water bath. The tubing exits the water bath and is inserted into a collection tube immersed in ice.

The flow rate is set at 0.4 mL/minute, and the total run time is 35 minutes for the 10.95 mL volume. After collecting the microspheres, the collection tube is spun at 3000 rpm for 20 minutes in a Beckman J613 centrifuge. A 2nd water wash is completed, and the microsphere pellets are spun down at 2600 rpm for 15 minutes. The final water is centrifuged at 1500 rpm for 15 minutes.

An aliquot is removed for particle size analysis by the Coulter LS 230. The microspheres are frozen at $-80°$ C., and placed in a lyophilizer for 2 days.

Figure 6:
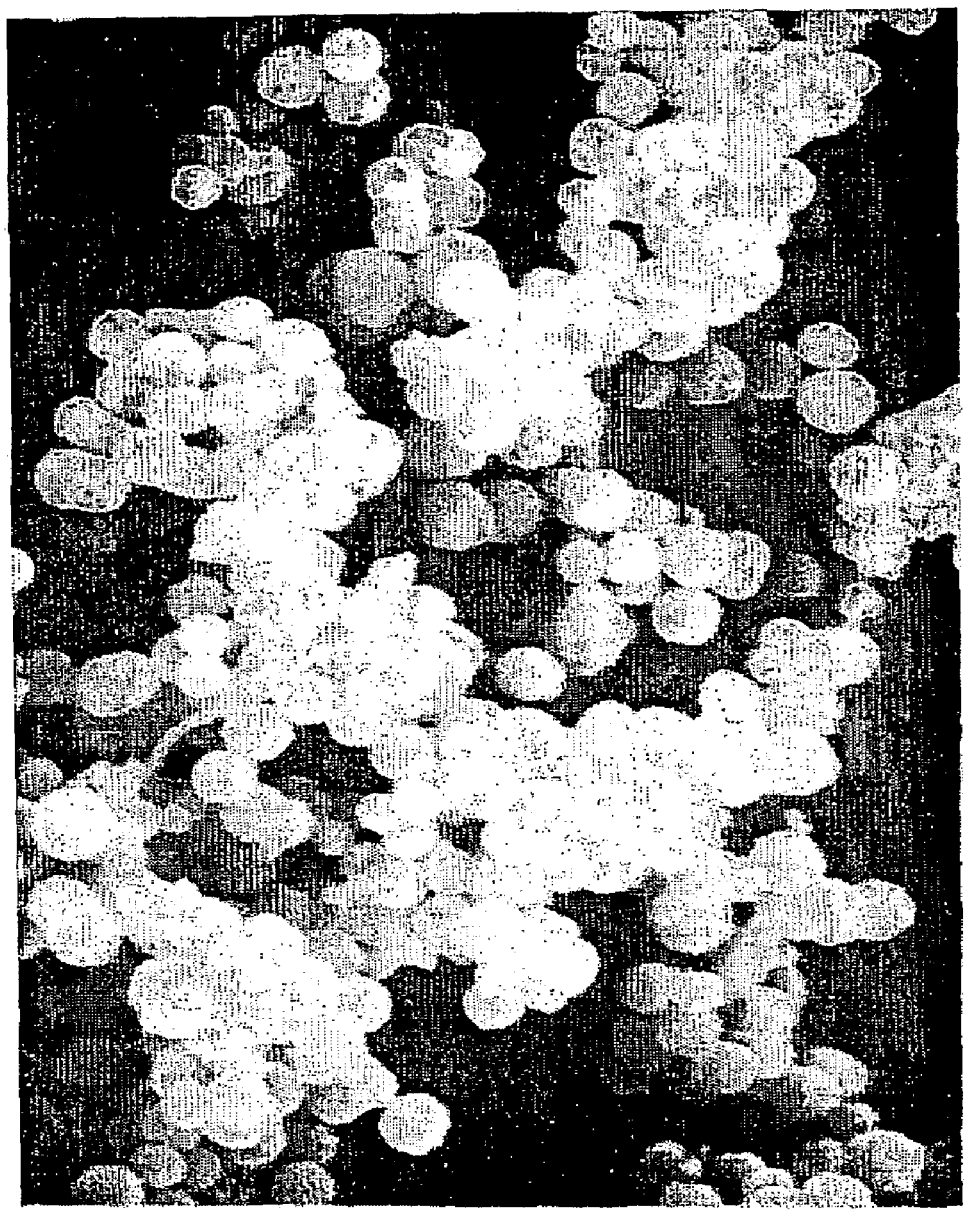
FIG. 6 is a scanning electron micrograph of insulin microspheres formed by a continuous flow process utilizing the method of this invention.

The particle size is determined to be 1.397 microns by volume, 1.119 microns by surface area, and 0.691 microns by number. FIG. 6 is a scanning electron micrograph which indicates uniform sized and non-aggregated insulin microspheres.

The use of the flow-through system, with the insulin exposed to 90° C. temperatures for a short time period, allows the production of particles which are 100% spherical microspheres. The final composition of the microspheres is virtually all protein (insulin) as determined by HPLC. These results are consistent with the observation that plastic and even glass shards that increase surface area to volume ratios result in the formation of microspheres rather than amorphous protein precipitates 70% of the starting material is incorporated into the insulin microspheres, as determined by the use of radio labeled insulin.

HPLC analysis of dissolved product indicates that the elution time of dissolved insulin microspheres is not significantly different from an insulin standard or the native insulin starting material.

EXAMPLE 4

Bioactivity of Insulin Microspheres

The bioactivity of insulin incorporated in the microspheres of this invention is demonstrated in the rat glucose depression model. The purpose of this experiment is to determine whether there is residual insulin bioactivity in the insulin microspheres of this invention. This is accomplished by injecting animals-with both dissolved microspheres, and suspended microspheres prepared from Zn insulin.

The following materials are used in this experiment:
8 male Fisher rats with an average weight of 264 grams
2×'s 2 mg of insulin microspheres deionized water
0.5 cc insulin syringes
AccuCheck Advantage glucose monitor (Roche Diagnostics)
AccuCheck Comfort Curve glucose strips The animals are divided into three groups: Group A, Group B and Group C. Each group contained three animals. The average weight of the animals in Group A is 262 grams. The average weight of the animals in Group B is 256 grams. The average weight of the animals in Group C is 280 grams. One mL of PBS is added to vial 1 and vortexed, and the particles are dissolved. One mL of deionized water is added to vial 2 and vortexed, and the particles remain in suspension. Each rat receives 200 µL of insulin (1 mg of insulin has 26 units of activity, and 1000 µL has 52 units). Group A receives the PBS solubilized insulin particles. Group B receives the suspended microspheres in deionized water. Group C receives 200 µL of saline solution.

Blood glucose results are based on pre-bleeds and post-bleed injection bleeds obtained by retro-orbital bleeding.

Figure 7:
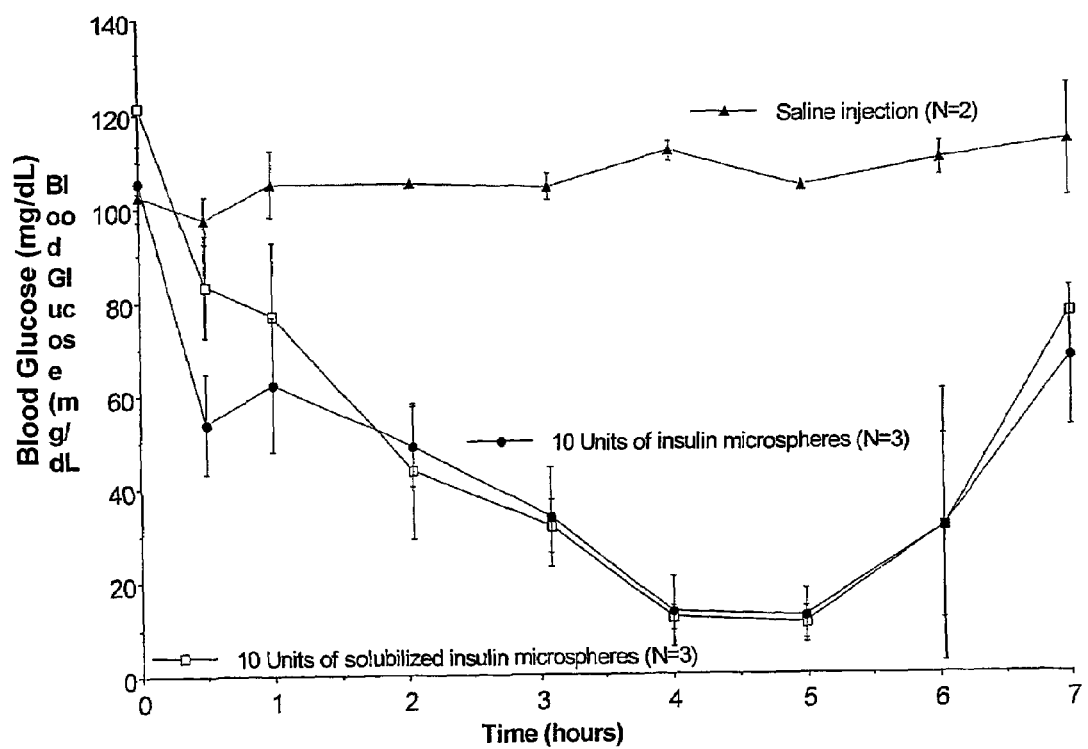
FIG. 7 is a graph showing the depression of blood glucose levels in rats. The blood glucose levels are plotted against the time after insulin injection for insulin microspheres and solubilized insulin microspheres. A saline control is also shown.

Glucose depression is demonstrated in both the insulin particle group and the solubilized insulin particle group as shown in FIG. 7. Normal rats do not show significant deviations in blood glucose from the pre-injection values.

Based on the foregoing, bioactivity of insulin incorporated in ProMaxx microspheres is clearly demonstrated in the rat blood glucose depression model. Blood glucose concentrations are depressed within 30 minutes of injection, and achieve their lowest levels 4 to 5 hours post injection.

Each of the foregoing patents, patent applications and references that are recited in this application are herein incorporated in their entirety by reference. Having described the presently preferred embodiments, and in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

What is claimed is:

1. A process for preparing microspheres comprising the steps of
combining a macromolecule and a polymer in an aqueous solution, wherein the polymer is water soluble or soluble in a water miscible solvent,
contacting a volume of the aqueous solution with a surface at a surface area to volume ratio of at least about 6.5 cm$^{-1}$,
heating the aqueous solution, and
forming the microspheres continuously in the aqueous solution in a continuous process.

2. The process of claim 1 wherein the surface area to volume ratio is at least about 14 cm$^{-1}$.

3. The process of claim 1 wherein the surface is a hydrophobic surface.

4. The process of claim 3 wherein the hydrophobic surface is formed from a material selected from metals, ceramics and glass.

5. The process of claim 4 wherein the metal is stainless steel.

6. The process of claim 3 wherein the hydrophobic surface is formed from a hydrophobic polymer.

7. The process of claim 6 wherein the hydrophobic polymer is selected from the group consisting of polypropylene, polystyrene, Teflon and silicone polymers.

8. The process of claim 1 wherein the macromolecule is selected from the group consisting of proteins, peptides, nucleic acids, carbohydrates, protein conjugates viruses, virus particles, and mixtures thereof.

9. The process of claim 8 wherein the macromolecule is a peptide.

10. The process of claim 9 wherein the peptide is a polypeptide.

11. The process of claim 8 wherein the macromolecule is a carbohydrate.

12. The process of claim 11 wherein the carbohydrate is a polysaccharide.

13. The process of claim 8 wherein the macromolecule is a protein.

14. The process of claim 13 wherein the protein is a therapeutic protein.

15. The process of claim 14 wherein the protein is selected from the group consisting of insulin, human serum albumin, human growth hormone, parathyroid hormone and calcitonin.

16. The process of claim 1 wherein the microspheres have a mean diameter in the range of from about 0.1 microns to about 10.0 microns.

17. The process of claim 16 wherein the microspheres have a mean diameter in the range of from about 0.5 microns to about 5.0 microns.

18. The process of claim 17 wherein the microspheres have a mean diameter in the range of from about 1.0 microns to about 2.0 microns.

19. The process of claim 1 wherein the aqueous solution of macromolecule and polymer is heated to a temperature in the range of from about 37° C. to about 95° C. for a time period of about 1 minute to about 24 hours.

20. The process of claim 1 wherein the polymer is selected from the group consisting of carbohydrate polymers, poly-aliphatic alcohols, poly(vinyl) polymers, polyacrylic acids, polyorganic acids, polyamino acids, polyethers, naturally occurring polymers, polyimides, polyesters, polyaldehydes, co-polymers, block co-polymers, terpolymers, surfactants, branched polymers, cyclo-polymers, and mixtures thereof.

21. The process of claim 20 wherein the polymer is selected from the group consisting of dextran, polyethylene glycol, polyvinyl pyrrolidone, co-polymers of polyethylene glycol and polyvinyl pyrrolidone, polyvinyl alcohol, co-polymers of polyoxyethylene and polyoxypropylene, and mixtures thereof.

22. The process of claim 21 wherein the polymer is a co-polymer of polyethylene glycol and polyvinyl pyrrolidone, or a co-polymer of polyoxyethylene and polyoxypropylene.

23. The process of claim 1 wherein the microspheres comprise greater than about 90% macromolecule by weight.

24. The process of claim 23 wherein the microspheres comprise greater than about 95% macromolecule by weight.

25. The process of claim 24 wherein the microspheres comprise greater than about 99% macromolecule by weight.

26. A product prepared according to the continuous process of claim 1.

27. The process of claim 1 wherein the contacting of the aqueous solution with the surface comprises moving the aqueous solution continuously over the surface.

28. The process of claim 27 wherein the aqueous solution is moved with a pump.

29. The process of claim 27 wherein the aqueous solution is moved at a speed of about 0.4 ml/minute.

30. The process of claim 1 wherein the surface is the inner surface of a tubing.

31. The process of claim 30 wherein the tubing has an inner diameter of 1/32 inches to 1/8 inches.

32. The process of claim 1 further comprising combining additional polymers with the macromolecule and the polymer in the aqueous solution.

33. The process of claim 1 wherein the heating comprises exposing the solution to heat, radiation or ionization.

34. The process of claim 33 wherein the radiation is microwave radiation.

35. The process of claim 33 wherein the heat, radiation or ionization is used in combination with sonication, vortexing, mixing or stifling.

36. The process of claim 1, further comprising allowing the microspheres to continuously flow through for collection.

* * * * *